(12) United States Patent
Komai

(10) Patent No.: US 12,390,563 B2
(45) Date of Patent: Aug. 19, 2025

(54) CLOT ADHESION PREVENTING AGENT AND BLOOD COLLECTION CONTAINER

(71) Applicant: SEKISUI MEDICAL CO., LTD., Tokyo (JP)

(72) Inventor: Kuniya Komai, Yamaguchi (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 1012 days.

(21) Appl. No.: 17/426,014

(22) PCT Filed: Jan. 29, 2020

(86) PCT No.: PCT/JP2020/003126
§ 371 (c)(1),
(2) Date: Jul. 27, 2021

(87) PCT Pub. No.: WO2020/158787
PCT Pub. Date: Aug. 6, 2020

(65) Prior Publication Data
US 2022/0133961 A1    May 5, 2022

(30) Foreign Application Priority Data

Feb. 1, 2019   (JP) .................. 2019-016753

(51) Int. Cl.
| | | |
|---|---|---|
| *A61L 33/00* | (2006.01) | |
| *A61B 5/15* | (2006.01) | |
| *A61L 33/02* | (2006.01) | |
| *A61L 33/04* | (2006.01) | |
| *A61L 33/06* | (2006.01) | |
| *A61L 33/12* | (2006.01) | |

(52) U.S. Cl.
CPC .... *A61L 33/0041* (2013.01); *A61B 5/150755* (2013.01); *A61L 33/027* (2013.01); *A61L 33/04* (2013.01); *A61L 33/062* (2013.01); *A61L 33/128* (2013.01)

(58) Field of Classification Search
CPC combination set(s) only.
See application file for complete search history.

(56) References Cited

U.S. PATENT DOCUMENTS

| | | |
|---|---|---|
| 5,306,270 A | 4/1994 | Macartney et al. |
| 2006/0171915 A1 | 8/2006 | Okamoto et al. |
| 2008/0274532 A1 | 11/2008 | Minamoto et al. |
| 2010/0248329 A1 | 9/2010 | Okamoto et al. |
| 2011/0144536 A1 | 6/2011 | Inoue et al. |
| 2012/0070350 A1 | 3/2012 | Aaraku et al. |
| 2012/0271010 A1 | 10/2012 | Sakaguchi et al. |
| 2012/0308446 A1 | 12/2012 | Inoue et al. |

FOREIGN PATENT DOCUMENTS

| | | |
|---|---|---|
| CN | 1761876 | 4/2006 |
| CN | 101137902 | 3/2008 |
| CN | 102132140 | 7/2011 |
| CN | 102656213 | 9/2012 |
| CN | 102741690 | 10/2012 |
| CN | 102770762 | 11/2012 |
| EP | 1 619 497 | 1/2006 |
| EP | 1 860 436 | 11/2007 |
| JP | 56-104644 | 8/1981 |
| JP | 2007-248175 | 9/2007 |
| JP | 2007-304004 | 11/2007 |
| JP | 2008-304207 | 12/2008 |
| JP | 2015-197362 | 11/2015 |
| KR | 10-2006-0011967 | 2/2006 |
| WO | 2010/024326 | 3/2010 |
| WO | 2011/105151 | 9/2011 |

OTHER PUBLICATIONS

Extended European Search Report dated Sep. 16, 2022 in European Patent Application No. 20748851.1.
International Preliminary Report on Patentability issued Jul. 27, 2021 in International (PCT) Application No. PCT/JP2020/003126.
International Search Report issued Mar. 17, 2020 in International (PCT) Application No. PCT/JP2020/003126.

*Primary Examiner* — Fereydoun G Sajjadi
*Assistant Examiner* — Qinhua Gu
(74) *Attorney, Agent, or Firm* — Wenderoth, Lind & Ponack, L.L.P.

(57) ABSTRACT

Provided is a clot adhesion preventing agent capable of suppressing adhesion of clot to the inner wall surface of a blood collection container. The clot adhesion preventing agent according to the present invention includes a polyether compound or a silicone oil, and an amino acid.

11 Claims, 1 Drawing Sheet

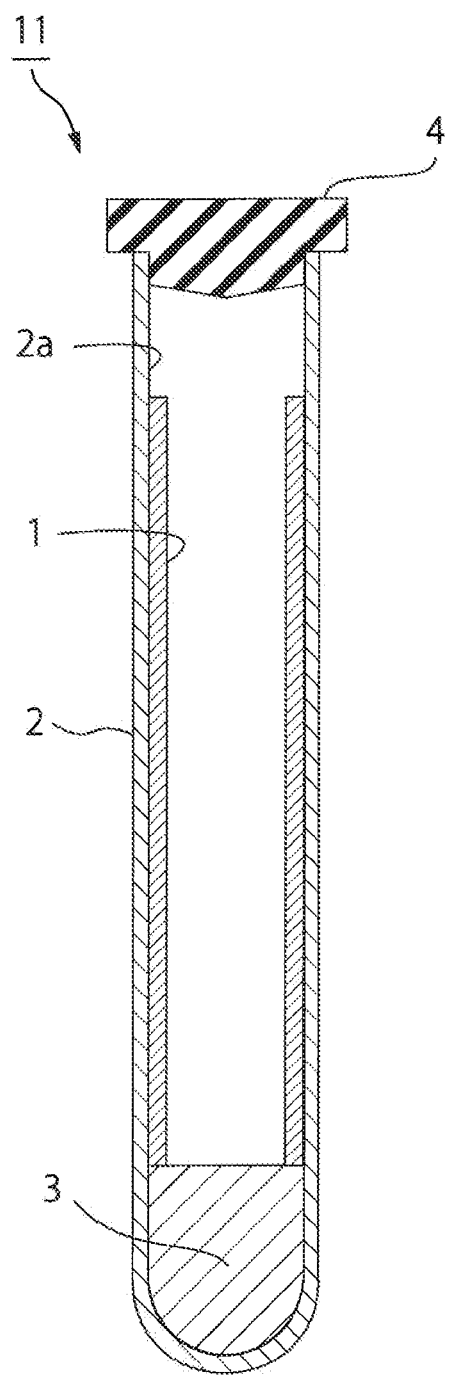

CLOT ADHESION PREVENTING AGENT AND BLOOD COLLECTION CONTAINER

TECHNICAL FIELD

The present invention relates to a clot adhesion preventing agent. The present invention also relates to a blood collection container including the clot adhesion preventing agent.

BACKGROUND ART

In clinical examinations, blood collection containers such as blood collection tubes are widely used to collect blood samples. Blood can be separated into serum and clot by collecting and coagulating blood in a blood collection container including a serum separating composition, followed by centrifugation. At this time, serum is located above the serum separating composition, and clot is located below the serum separating composition.

By using a blood collection container coated with a component by which clot does not easily adhere, it is possible to prevent clot from adhering to the inner wall surface of the blood collection container above the serum separating composition after centrifugation.

As the component by which clot does not easily adhere, a silicone oil and the like are described in Patent Document 1 described below.

RELATED ART DOCUMENT

Patent Document

Patent Document 1: JP S56-104644 A

SUMMARY OF THE INVENTION

Problems to be Solved by the Invention

In a conventional blood collection container, after blood is separated into serum and clot, the clot may adhere to the inner wall surface of the blood collection container above the serum separating composition. When a layer including a component by which clot does not easily adhere, such as a silicone oil as described in Patent Document 1, is present on the inner wall surface of a blood collection container, it is possible to suppress adhesion of clot to the inner wall surface to some extent. However, such an effect may not be sufficient.

In addition, when the amount of a silicone oil or the like is simply increased for the purpose of sufficiently suppressing adhesion of clot, the silicone oil or the like may peel off from the inner wall surface of the blood collection container, and then float as oil droplets or an oil film on the serum surface. When the oil droplets or oil film adhere(s) to a sample suction nozzle of an automatic analyzer, the nozzle may be narrowed or blocked, so that accurate sample suction may be prevented.

When clot adhering to the inner wall surface of the blood collection container comes into contact with serum, the components derived from blood cells in the clot may be mixed into the serum, so that the measurement accuracy is lowered in a test performed using the serum. For example, when clot adhering to the inner wall surface of the blood collection container comes into contact t with serum, the contents from blood cell components in the clot may be mixed into the serum etc., so that hemolysis occurs in the serum. As a result, the test values for potassium and the like may be affected. In addition, for example, when clot adhering to the inner wall surface of the blood collection container comes into contact with serum, the components in the serum may be taken up into blood cells, so that the concentration of the components in the serum changes. As a result, the test values for the components may be affected.

An object of the present invention is to provide a clot adhesion preventing agent capable of suppressing adhesion of clot to the inner wall surface of a blood collection container. Another object of the present invention is to provide a blood collection container including the clot adhesion preventing agent.

Means for Solving the Problems

According to a broad aspect of the present invention, there is provided a clot adhesion preventing agent including a polyether compound or a silicone oil, and an amino acid.

In a certain aspect of the clot adhesion preventing agent according to the present invention, the clot adhesion preventing agent includes the polyether compound.

In a certain aspect of the clot adhesion preventing agent according to the present invention, the polyether compound is polypropylene glycol or a polypropylene glycol derivative.

In a certain aspect of the clot adhesion preventing agent according to the present invention, the clot adhesion preventing agent includes the silicone oil.

In a certain aspect of the clot adhesion preventing agent according to the present invention, the silicone oil is a modified silicone oil.

In a certain aspect of the clot adhesion preventing agent according to the present invention, the amino acid includes alanine, glycine, asparagine or serine.

In a certain aspect of the clot adhesion preventing agent according to the present invention, the amino acid is β-alanine.

In a certain aspect of the clot adhesion preventing agent according to the present invention, the clot adhesion preventing agent includes a blood coagulation promoting component.

In a certain aspect of the clot adhesion preventing agent according to the present invention, the blood coagulation promoting component includes silica powder.

In a certain aspect of the clot adhesion preventing agent according to the present invention, the blood coagulation promoting component includes thrombin or a thrombin-like enzyme.

According to a broad aspect of the present invention, there is provided a blood collection container, including a blood collection container main body and a clot adhesion preventing layer disposed on the inner wall surface of the blood collection container main body, the clot adhesion preventing layer being made of the clot adhesion preventing agent.

In a certain aspect of the blood collection container according to the present invention, the blood collection container includes a serum separating composition contained in the bottom of the blood collection container main body.

Effect of the Invention

Because the clot adhesion preventing agent according to the present invention includes a polyether compound or a silicone oil, and an amino acid, it is possible to suppress adhesion of clot to the inner wall surface of a blood collection container.

BRIEF DESCRIPTION OF DRAWINGS

FIG. 1 is a front sectional view schematically showing a blood collection container including the clot adhesion preventing agent according to one embodiment of the present invention.

MODES FOR CARRYING OUT THE INVENTION

Hereinafter, the present invention is described in detail.

The clot adhesion preventing agent according to the present invention includes a polyether compound or a silicone oil, and an amino acid.

The clot adhesion preventing agent according to the present invention may include a polyether compound, a silicone oil, or both a polyether compound and a silicone oil.

Because the clot adhesion preventing agent according to the present invention includes the above composition, it is possible to suppress adhesion of clot to the inner wall surface of a blood collection container. The clot adhesion preventing agent according to the present invention can suppress adhesion of clot to the inner wall surface of a blood collection container without increasing the amount of a conventionally known clot adhesion preventing component such as a silicone oil.

In addition, by the clot adhesion preventing agent according to the present invention, the clot adhesion preventing agent is less likely to peel off from the inner wall surface of a blood collection container, and is less likely to float as oil droplets or an oil film on the serum surface.

Hereinafter, each component used in the clot adhesion preventing agent of the present invention is described in detail.

(Polyether Compound)

As the polyether compound, conventionally known polyether compounds can be used. The polyether compound may be used alone or in combination of two or more.

Examples of the polyether compound include polyoxyalkylene glycols, polyoxyalkylene glycol derivatives and poorly water-soluble polyoxyalkylene derivative.

Examples of the polyoxyalkylene glycols include polytetramethylene ether glycol, polyethylene glycol, polyethylene oxide, polypropylene glycol, polyoxyethylene polyoxypropylene glycol and polyvinyl alcohol.

Examples of the polyoxyalkylene glycol derivatives include polyoxyalkylene glycol ethers such as polypropylene glycol derivatives, and polyoxyalkylene alkyl ethers.

Examples of the polypropylene glycol derivatives include polyoxypropylene glyceryl ether, polypropylene glycol dimethyl ether, polyoxyethylene polyoxypropylene alkyl ether, polyoxyethylene polyoxypropylene glycol and polyoxypropylene alkyl ether.

Examples of the poorly water-soluble polyoxyalkylene derivatives include derivatives derivatized by introducing various compounds into conventionally known polyoxyalkylene. Examples of the poorly water-soluble polyoxyalkylene derivatives include a butanol derivative of polyoxyalkylene and a glycerin derivative of polyoxyalkylene.

From the viewpoint of more effectively suppressing adhesion of clot, the polyether compound is preferably a polyether-based surfactant.

From the viewpoint of even more effectively suppressing adhesion of clot, the polyether compound is preferably a polyalkylene glycol or a polyalkylene glycol derivative, more preferably polypropylene glycol or a polypropylene glycol derivative.

When the clot adhesion preventing agent includes the polyether compound, the content of the polyether compound in 100% by weight of the clot adhesion preventing agent is preferably 0.01% by weight or more, more preferably 0.1% by weight or more, and preferably 10% by weight or less, more preferably 5% by weight or less. When the content of the polyether compound is the above lower limit or more, adhesion of clot can be suppressed even more effectively. When the content of the polyether compound is the above upper limit or less, generation of oil droplets, an oil film or the like on the serum surface can be effectively suppressed.

(Silicone Oil)

As the silicone oil, conventionally known silicone oils can be used. The silicone oil may be used alone or in combination of two or more.

Examples of the silicone oil include aliphatic silicone oils such as dimethylpolysiloxane and methylhydrodienepolysiloxane, and aromatic silicone oils such as methylphenylpolysiloxane.

The silicone oil may be a modified silicone oil which is modified to be hydrophilic via introduction of a polar group. Examples of the polar group include a hydroxyl group, an amino group, a carboxyl group, an epoxy group and an ether group.

From the viewpoint of more effectively suppressing adhesion of clot, the silicone oil is preferably a modified silicone oil.

From the viewpoint of even more effectively suppressing adhesion of clot, the silicone oil is preferably a silicone oil-based surfactant.

The silicone oil is preferably dimethylpolysiloxane or modified dimethylpolysiloxane, more preferably modified dimethylpolysiloxane, even more preferably modified dimethylpolysiloxane having an ether group or an amino group, particularly preferably a modified dimethylpolysiloxane having an ether group. In this case, adhesion of clot can be suppressed even more effectively.

Examples of commercial products of the modified dimethylpolysiloxane having an ether group include BY16-201, SF8410, SF8427, SF8428, FZ-2162, SH3746, SH3749, FZ-77, L-7001, Y7006, FZ-2104, FZ-2110, SH8400, SH8410, SH3773M, FZ-2207, FZ-2203, FZ-2222 and FZ-2208 (manufactured by Dow Toray Co., Ltd.).

When the clot adhesion preventing agent includes the silicone oil, the content of the silicone oil in 100% by weight of the clot adhesion preventing agent is preferably 0.01% by weight or more, more preferably 0.1% by weight or more, and preferably 10% by weight or less, more preferably 5% by weight or less. When the content of the silicone oil is the above lower limit or more, adhesion of clot can be suppressed even more effectively. When the content of the silicone oil is the above upper limit or less, generation of oil droplets, an oil film or the like on the serum surface can be effectively suppressed.

The total content of the polyether compound and the silicone oil in 100% by weight of the clot adhesion preventing agent is preferably 0.01% by weight or more, more preferably 0.1% by weight or more, and preferably 10% by weight or less, more preferably 5% by weight or less. When the total content is the above lower limit or more, adhesion of clot can be suppressed even more effectively. When the total content is the above upper limit or less, generation of oil droplets, an oil film or the like in serum can be effectively suppressed.

(Amino Acid)

The clot adhesion preventing agent includes an amino acid. As the amino acid, conventionally known amino acids can be used. The amino acid may be used alone or in combination of two or more.

Examples of the amino acid include hydrophilic amino acids such as arginine, asparagine, aspartic acid, glutamine, glutamic acid, histidine, lysine, serine and threonine, and hydrophobic amino acids such as alanine, glycine, cysteine, isoleucine, leucine, methionine, phenylalanine, proline, tryptophan, tyrosine and valine.

The amino acid may be a hydrophilic amino acid or a hydrophobic amino acid. In addition, the amino acid may be a D-amino acid or an L-amino acid. In addition, the amino acid may be an α-amino acid or a β-amino acid.

From the viewpoint of even more effectively suppressing adhesion of clot, the amino acid preferably alanine, glycine, asparagine or serine, more includes preferably includes alanine or asparagine.

From the viewpoint of even more effectively suppressing adhesion of clot, the amino acid is preferably β-alanine.

The content of the amino acid in 100% by weight of the clot adhesion preventing agent is preferably 0.5% by weight or more, more preferably 1% by weight or more, and preferably 10% by weight or less, more preferably 5% by weight or less. When the content of the amino acid is the above lower limit or more, adhesion of clot can be suppressed even more effectively. When the content of the amino acid is the above upper limit or less, the clot adhesion preventing agent is less likely to precipitate when applied to the inner wall surface of a blood collection container, so that a coating nozzle is less likely to be blocked.

When the clot adhesion preventing agent includes the polyether compound, the weight ratio of the content of the amino acid to the content of the polyether compound (content of the amino acid/content of the polyether compound) is preferably 1 or more, more preferably 3 or more, still more preferably 5 or more, and preferably 15 or less. When the weight ratio is the above lower limit or more and the above upper limit or less, adhesion of clot can be suppressed even more effectively.

When the clot adhesion preventing agent includes the silicone oil, the weight ratio of the content of the amino acid to the content of the silicone oil (content of the amino acid/content of the silicone oil) is preferably 1 or more, more preferably 3 or more, still more preferably 5 or more, and preferably 15 or less. When the weight ratio is the above lower limit or more and the above upper limit or less, adhesion of clot can be suppressed even more effectively.

The weight ratio of the content of the amino acid to the total content of the polyether compound and the silicone oil (content of the amino acid/total content of the polyether compound and the silicone oil) is preferably 1 or more, more preferably 3 or more, still more preferably 5 or more, and preferably 15 or less. When the weight ratio is the above lower limit or more and the above upper limit or less, adhesion of clot can be suppressed even more effectively.

[Blood Coagulation Promoting Component]

The clot adhesion preventing agent may include a blood coagulation promoting component. When the clot adhesion preventing agent includes a blood coagulation promoting component, blood coagulation can be promoted and the blood coagulation time can be shortened.

As the blood coagulation promoting component, conventionally known blood coagulation promoting components can be used. Examples of the blood coagulation promoting component include inorganic powder, thrombin and thrombin-like enzymes such as snake venom. The blood coagulation promoting component may be used alone or in combination of two or more.

From the viewpoint of effectively coagulating blood, the blood coagulation promoting component preferably includes inorganic powder, thrombin or a thrombin-like enzyme.

Examples of the inorganic powder include silica powder, glass powder, kaolin powder, celite powder and bentonite powder.

From the viewpoint of coagulating blood well, the inorganic powder is preferably silica powder.

The average particle diameter of the inorganic powder is preferably 10 nm or more, more preferably 100 nm or more, and preferably 1 mm or less, more preferably 100 μm or less. When the average particle diameter of the inorganic powder is the above lower limit or more and the above upper limit or less, blood can be coagulated well in a short time. When the average particle diameter of the inorganic powder is the above upper limit or less, precipitation of the inorganic powder in the clot adhesion preventing agent can be effectively suppressed.

As the average particle diameter of the inorganic powder, a value of median diameter of 50% (d50) is adopted. The average particle diameter can be measured using a laser diffraction/scattering type particle size distribution measuring device.

The content of the inorganic powder in 100% by weight of the clot adhesion preventing agent is preferably 0.5% by weight or more, more preferably 1% by weight or more, and preferably 10% by weight or less, more preferably 5% by weight or less. When the content of the inorganic powder is the above lower limit or more, blood can be coagulated well in a short time. When the content of the inorganic powder is the above upper limit or less, precipitation of the inorganic powder in the clot adhesion preventing agent can be effectively suppressed.

The content of the thrombin and the thrombin-like enzyme in 100% by weight of the clot adhesion preventing agent can be appropriately changed.

[Solvent]

The clot adhesion preventing agent preferably includes a solvent. By using the solvent, the viscosity of the clot adhesion preventing agent can be controlled in a suitable range, and the coatability of the clot adhesion preventing agent can be improved. The solvent may be used alone or in combination of two or more.

Examples of the solvent include water, methanol, ethanol, butanol, isopropanol and hexane.

The content of the solvent in the clot adhesion preventing agent is not particularly limited. The content of the solvent can be appropriately changed in consideration of the coatability of the clot adhesion preventing agent.

[Other Components]

For the purpose of improving the adhesion to a blood collection container, coatability, blood coagulation performance and the like, the clot adhesion preventing agent may include other components such as a water-soluble binder, a protease inhibitor and an antifibrinolytic agent. The respective other components may be used alone or in combination of two or more.

Examples of the water-soluble binder include polyvinyl alcohol, polyvinylpyrrolidone, acrylic acid-based copolymers and polyoxyalkylene block copolymers.

Examples of the protease inhibitor include aprotinin and a soybean trypsin inhibitor.

Examples of the antifibrinolytic agent include ε-aminocaproic acid, aminomethylbenzoic acid and aminomethylcyclohexanecarboxylic acid.

(Other Details of Clot Adhesion Preventing Agent)

The clot adhesion preventing agent according to the present invention is preferably applied to the inner wall surface of a blood collection container main body. The clot adhesion preventing agent according to the present invention is suitably used for forming a clot adhesion preventing layer on a blood collection container.

The clot adhesion preventing agent can be produced by, for example, mixing the above-mentioned polyether compound or silicone oil, amino acid, blood coagulation promoting component, other component and solvent.

(Blood Collection Container)

The blood collection container includes a blood collection container main body and a clot adhesion preventing layer formed on the inner wall surface of the blood collection container main body, and the clot adhesion preventing layer is made of the clot adhesion preventing agent.

The material of the blood collection container main body is not particularly limited. Examples of the material of the blood collection container main body include glass, polyethylene terephthalate and polypropylene.

The blood collection container main body preferably has an open end at one end. The other end of the blood collection container main body is preferably closed.

The blood collection container can be produced by coating the inner wall surface of the blood collection container main body with the clot adhesion preventing agent. The coating method is not particularly limited. Examples of the coating method include spray coating and dipping coating method. The clot adhesion preventing layer is preferably formed by coating the inner wall surface of the blood collection container main body with the clot adhesion preventing agent, followed by drying to remove the solvent.

Accordingly, the clot adhesion preventing layer is preferably a layer from which the solvent in the clot adhesion preventing agent has been removed. The clot adhesion preventing layer is preferably a dried product layer of the clot adhesion preventing agent.

The clot adhesion preventing layer may be entirely formed on the inner wall surface of the blood collection container main body. The clot adhesion preventing layer is preferably formed on the inner wall surface of the side surface portion of the blood collection container main body. The clot adhesion preventing layer may be entirely formed on the inner wall surface of the side surface portion of the blood collection container, or may be partially formed thereon.

The clot adhesion preventing layer may be a continuous layer or a discontinuous layer. The clot adhesion preventing layer may be formed in a dispersed state on the inner wall surface of the blood collection container main body. The clot adhesion preventing layer may be formed in an island state such as a dot state on the inner wall surface of the blood collection container main body. As described above, even in the case of a discontinuous layer formed on the inner wall surface of the blood collection container main body in a dispersed state or formed in an island state, the discontinuous layer is regarded as a layer in the present invention.

When the clot adhesion preventing layer includes the polyether compound, in the clot adhesion preventing layer, the weight ratio of the content of the amino acid to the content of the polyether compound (content of the amino acid/content of the polyether compound) is preferably 1 or more, more preferably 3 or more, still more preferably 5 or more, and preferably 15 or less. When the weight ratio is the above lower limit or more and the above upper limit or less, adhesion of clot can be suppressed even more effectively.

When the clot adhesion preventing layer includes the silicone oil, in the clot adhesion preventing layer, the weight ratio of the content of the amino acid to the content of the silicone oil (content of the amino acid/content of the silicone oil) is preferably 1 or more, more preferably 3 or more, still more preferably 5 or more, and preferably 15 or less. When the weight ratio is the above lower limit or more and the above upper limit or less, adhesion of clot can be suppressed even more effectively.

In the clot adhesion preventing layer, the weight ratio of the content of the amino acid to the total content of the polyether compound and the silicone oil (content of the amino acid/total content of the polyether compound and the silicone oil) is preferably 1 or more, more preferably 3 or more, still more preferably 5 or more, and preferably 15 or less. When the weight ratio is the above lower limit or more and the above upper limit or less, adhesion of clot can be suppressed even more effectively.

The blood collection container preferably includes a serum separating composition contained in the bottom of the blood collection container main body.

As the serum separating composition, conventionally known serum separating compositions can be used. Examples of the serum separating composition include serum separating compositions described in WO 2011/105151 A1 and the like.

The serum separating composition is used for the purpose of preventing component transfer between the clot layer and the serum layer by moving to a position between the serum layer and the clot layer to form a partition wall during centrifugation.

The blood collection container preferably includes a stopper. As the stopper, conventionally known stoppers can be used. The stopper may include a stopper main body such as a rubber stopper, and a cap member.

FIG. 1 is a front sectional view schematically showing a blood collection container including the clot adhesion preventing agent according to one embodiment of the present invention.

The blood collection container 11 shown in FIG. 1 includes a blood collection container main body 2, a clot adhesion preventing layer 1, a serum separating composition 3 and a stopper 4. The clot adhesion preventing layer 1 is formed on the inner wall surface 2a of the side surface of the blood collection container main body 2. The serum separating composition 3 is contained in the bottom of the blood collection container main body 2. The stopper 4 is attached to an open end of the blood collection container main body 2. The clot adhesion preventing layer may be entirely formed on the inner wall surface of the blood collection container main body, or may be partially formed thereon. In addition, as described above, the clot adhesion preventing layer may be formed in a dispersed state on the inner wall surface of the blood collection container main body, or may be formed in an island state such as a dot state on the inner wall surface of the blood collection container main body.

The blood collection container main body is preferably a blood collection tube main body. The blood collection container is preferably a blood collection tube.

The internal pressure in the blood collection container is not particularly limited. The blood collection container may be a vacuum blood collection container (vacuum blood collection tube) that has been sealed with the stopper after the gas is discharged from the inside. In the case of a vacuum blood collection tube, a certain amount of blood can be easily collected regardless of the technical difference between blood collectors.

From the viewpoint of preventing bacterial infection, the inside of the blood collection container is preferably sterilized in accordance with the ISO and JIS standards.

When separating serum from blood, blood is collected into a blood collection container containing a serum separating composition, and then centrifuged by a centrifuge causes cell device. Centrifugation components, blood coagulation components and the like in the blood to settle down (clot), and serum to be separated as a supernatant. At this time, the serum separating composition is located in an intermediate layer between them to form a partition wall by which the clot and the serum are partitioned.

Hereinafter, the present invention is specifically described with reference to Examples and Comparative Examples. The present invention is not limited to the following Examples.

The following blood collection container main body was prepared.

A blood collection container main body having the shape shown in FIG. 1

Inner diameter 10.8 mm×length 100 mm (length: distance between one end (open end) and the other end)

Material: polyethylene terephthalate

The following stopper was prepared.

A stopper having the shape shown in FIG. 1

Stopper main body: rubber stopper (material: butyl rubber)

A serum separating composition was prepared as follows.

A liquid resin component was prepared by dissolving a cyclopentadiene-based oligomer (manufactured by Exxon Mobil Corporation, trade name: ESCOREZ 5690) and trimellitic acid ester (manufactured by Dainippon Ink and Chemicals, Inc., trade name: Monosizer W700) at 130° C. In this liquid resin component, polypropylene polyether (manufactured by NOF Corporation, trade name: Uniol D700) was dissolved as a polyalkylene polyether, followed by cooling to about 30° C. Next, hydrophilic fine powder silica (manufactured by Nippon Aerosil Co., Ltd., trade name: Aerosil 200CF) and hydrophobic fine powder silica (manufactured by Nippon Aerosil Co., Ltd., trade name: Aerosil R974) were added as inorganic powder into the liquid resin component, followed by stirring with a planetary mixer to be dispersed. In this way, the serum separating composition was prepared.

Materials for the following clot adhesion preventing agent were prepared.

(Polyether Compound)

Polypropylene glycol (manufactured by ADEKA Corporation, "ADEKA Polyether G4000") (Silicone oil)

Modified dimethylpolysiloxane having an ether group (manufactured by Dow Toray Co., Ltd., "SF8410")

(Amino Acid)

β-alanine

L-asparagine

L-serine

L-glycine (Blood Coagulation Promoting Component)

Silica powder (average particle diameter 5 μm)

EXAMPLE 1

Preparation of Clot Adhesion Preventing Agent

Polypropylene glycol, β-alanine, silica powder and water (solvent) were mixed in the amounts shown in Table 1 to prepare a clot adhesion preventing agent.

Preparation of Blood Collection Container

In the bottom of the blood collection container main body, 0.9 g of the serum separating composition was contained. Next, the inner wall surface of the blood collection container main body was spray-coated with the obtained clot adhesion preventing agent, followed by drying to form a clot adhesion preventing layer. Next, the blood collection container main body was depressurized to 12 kPa and then sealed with a stopper to prepare a blood collection container.

EXAMPLES 2 TO 7

Clot adhesion preventing agents and blood collection containers were prepared in the same manner as in Example 1 except that the composition of the clot adhesion preventing agent was changed as shown in Table 1.

COMPARATIVE EXAMPLE 1

A clot adhesion preventing agent and a blood collection container were prepared in the same manner as in Example 1 except that amino acids were not used.

COMPARATIVE EXAMPLE 2

A clot adhesion preventing agent and a blood collection container were prepared in the same manner as in Example 7 except that amino acids were not used.

(Evaluation)

(1) Amount of Clot Adhesion

In the obtained blood collection container, 1 mL of blood was collected and mixed with inversion, causing the blood to adhere to the entire inner wall surface of the blood collection container. Centrifugation was performed at 1500 G for 10 minutes by a centrifuge device. In the blood collection container after the centrifugation, serum was located at an upper position, clot was located at a lower position, and the serum separating composition was located in an intermediate layer between them to form a partition wall by which the clot and the serum were partitioned.

The blood collection container was opened, and the serum was removed. Subsequently, 0.5 mL of water was added, and the blood collection container was sealed again with a rubber stopper. Thereafter, mixing was performed with inversion, and then clot adhering to the inner wall surface of the blood collection container was hemolyzed in the added water. Subsequently, the resultant liquid was recovered.

The absorbance of the recovered liquid at a wavelength of 415 nm was measured using an automatic analyzer (manufactured by Hitachi High-Tech Corporation, "7170S").

The larger the absorbance value, the more blood cell components are hemolyzed in the recovered liquid. In other words, the larger the absorbance value, the larger the amount of clot adhering to the inner wall surface of the blood collection container after the centrifugation. Therefore, the smaller the absorbance value, the better the clot adhesion preventing effect.

The compositions and results are shown in Table 1 below.

[Table 1]

TABLE 1

|  |  |  | % | Example 1 | Example 2 | Example 3 | Example 4 | Example 5 |
|---|---|---|---|---|---|---|---|---|
| Composition of clot adhesion preventing agent | Polyether compound | Polypropylene glycol | % by weight | 0.3 | 0.3 | 0.3 | 0.3 | 0.3 |
|  | Silicone oil | Modified dimethylpolysiloxane having ether group | % by weight | — | — | — | — | — |
|  | Amino acid | β-alanine | % by weight | 0.5 | 2 | 4 | — | — |
|  |  | L-asparagine | % by weight | — | — | — | 2 | — |
|  |  | L-serine | % by weight | — | — | — | — | 2 |
|  |  | L-glycine | % by weight | — | — | — | — | — |
|  | Blood coagulation promoting component | Silica powder | % by weight | 2.5 | 2.5 | 2.5 | 2.5 | 2.5 |
|  | Solvent | Water | % by weight | 96.7 | 95.2 | 93.2 | 95.2 | 95.2 |
|  |  | Total | % by weight | 100 | 100 | 100 | 100 | 100 |
|  | Weight ratio (content of amino acid/content of polyether compound) or weight ratio (content of amino acid/content of silicone oil) |  |  | — | 1.7 | 6.7 | 13.3 | 6.7 | 6.7 |
| Evaluation | Amount of clot adhesion | Absorbance |  | — | 20200 | 13700 | 12900 | 14500 | 19400 |

|  |  |  |  | Example 6 | Example 7 | Comparative Example 1 | Comparative Example 2 |
|---|---|---|---|---|---|---|---|
| Composition of clot adhesion preventing agent | Polyether compound | Polypropylene glycol | % by weight | 0.3 | — | 0.3 | — |
|  | Silicone oil | Modified dimethylpolysiloxane having ether group | % by weight | — | 0.3 | — | 0.3 |
|  | Amino acid | β-alanine | % by weight | — | 2 | — | — |
|  |  | L-asparagine | % by weight | — | — | — | — |
|  |  | L-serine | % by weight | — | — | — | — |
|  |  | L-glycine | % by weight | 2 | — | — | — |
|  | Blood coagulation promoting component | Silica powder | % by weight | 2.5 | 2.5 | 2.5 | 2.5 |
|  | Solvent | Water | % by weight | 95.2 | 95.2 | 97.2 | 97.2 |
|  |  | Total | % by weight | 100 | 100 | 100 | 100 |
|  | Weight ratio (content of amino acid/content of polyether compound) or weight ratio (content of amino acid/content of silicone oil) |  |  | — | 6.7 | 6.7 | — | — |
| Evaluation | Amount of clot adhesion | Absorbance |  | — | 25200 | 15300 | 31300 | 42000 |

EXPLANATION OF SYMBOLS

1: Clot adhesion preventing layer
2: Blood collection container main body
2a: Inner wall surface
3: Serum separating composition
4: Stopper
11: Blood collection container

The invention claimed is:

1. A clot adhesion preventing agent, comprising a polyether compound or a silicone oil, and an amino acid, wherein the amino acid is an alanine or asparagine, wherein, when the clot adhesion preventing agent comprises the polyether compound, the weight ratio of the content of the amino acid to the content of the polyether compound is 3 or more and 15 or less, and wherein, when the clot adhesion preventing agent comprises the silicone oil, the weight ratio of the content of the amino acid to the content of the silicone oil is 3 or more and 15 or less.

2. The clot adhesion preventing agent according to claim 1, comprising the polyether compound.

3. The clot adhesion preventing agent according to claim 1, the polyether compound being polypropylene glycol or a polypropylene glycol derivative.

4. The clot adhesion preventing agent according to claim 1, comprising the silicone oil.

5. The clot adhesion preventing agent according to claim 1, the silicone oil being a modified silicone oil.

6. The clot adhesion preventing agent according to claim 1, the amino acid being β-alanine.

7. The clot adhesion preventing agent according to claim 1, comprising a blood coagulation promoting component.

8. The clot adhesion preventing agent according to claim 7, the blood coagulation promoting component comprising silica powder.

9. The clot adhesion preventing agent according to claim 7, the blood coagulation promoting component comprising thrombin or a thrombin-like enzyme.

10. A blood collection container, comprising
a blood collection container main body and
a clot adhesion preventing layer disposed on an inner wall surface of the blood collection container main body,
the clot adhesion preventing layer being made of the clot adhesion preventing agent according to claim 1.

11. The blood collection container according to claim 10, comprising a serum separating composition contained in a bottom of the blood collection container main body.

\* \* \* \* \*